United States Patent
Aronov et al.

(10) Patent No.: US 7,169,800 B2
(45) Date of Patent: Jan. 30, 2007

(54) IMIDAZOLE COMPOSITIONS USEFUL AS INHIBITORS OF PROTEIN KINASES

(75) Inventors: Alex Aronov, Watertown, MA (US); David J. Lauffer, Stow, MA (US); Pan Li, Arlington, MA (US); Ronald C. Tomlinson, Sudbury, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 117 days.

(21) Appl. No.: 10/949,027

(22) Filed: Sep. 24, 2004

(65) Prior Publication Data

US 2005/0148574 A1 Jul. 7, 2005

Related U.S. Application Data

(60) Provisional application No. 60/505,634, filed on Sep. 24, 2003.

(51) Int. Cl.
*A61K 31/422* (2006.01)
*C07D 413/04* (2006.01)

(52) U.S. Cl. ...................... 514/378; 548/247
(58) Field of Classification Search ................ 548/247; 514/378

See application file for complete search history.

(56) References Cited

FOREIGN PATENT DOCUMENTS

WO WO 00/62778 A1 10/2000
WO WO 03/022274 A2 3/2003

OTHER PUBLICATIONS

Golub et al., Science, vol. 286, Oct. 15, 1999, pp. 531-537.*
Christensen et al., A selective small molecule inhibitor of c-Met kinase inhibits c-Met-dependent phenotypes in vitro and exhibits cytoreductive antitumor activity in vivo. *Cancer Research* 63(21): 7345-55, 2003.

Jiang et al., Reduction of stromal fibroblast-induced mammary tumor growth, by retroviral ribozyme transgenes to hepatocyte growth factor/scatter factor and its receptor, c-MET, *Clinical Cancer Research* 9(11): 4274-81, 2003.

Abounader et al., Reversion of human glioblastoma malignancy by U1 small nuclear RNA/ribozyme targeting of scather factor/hepatocyte growth factor and c-met expression, *Journal of the National Cancer Institute* 91(18):, 1548-1556, 1999.

Davies et al., Targeting the HGF/SF receptor c-met using a hammerhead ribozyme transgene reduces in vitro invasion and migration in prostate cancer cells, *Prostate* 60: 317-324, 2004.

Matsumoto et al., NK4 (HGF-antagonist/angiogenesis inhibitor) in cancer biology and therapeutics, *Cancer Science* 94(4): 321-7, 2003.

Brockmann et al., Inhibition of intracerebral glioblastoma growth by local treatment with the scatter factor/hepatocyte growth factor-antagonist NK4, *Clinical Cancer Research* 9(12): 4578-85, 2003.

Wen et al., Hepatic gene expression of NK4, an HGF-antagonist/angiogenesis inhibitor, suppresses liver metastasis and invasive growth of colon cancer in mice, *Cancer Gene Therapy* 2004: 1-12, 2004.

Malaviya et al., Treatment of allergic asthma by targeting janus kinase 3-dependent leukotriene synthesis in mast cells with 4-(3',5'-dibromo-4'-hydroxyphenyl)amino-6,7-dimethoxyquinazoline (WHI-P97), *Journal Pharmacology and Experimental Therapeutics*, 295(3): 912-26, 2000.

* cited by examiner

*Primary Examiner*—Laura L. Stockton
(74) *Attorney, Agent, or Firm*—Daniel A. Pearson; Vertex Pharmaceuticals Incorporated

(57) ABSTRACT

The present invention relates to compounds useful of inhibitors of protein kinases. The invention also provides processes for preparing the compounds of this invention, pharmaceutically acceptable compositions comprising the compounds of the invention, and methods of using the compositions in the treatment of various disorders.

24 Claims, No Drawings

IMIDAZOLE COMPOSITIONS USEFUL AS INHIBITORS OF PROTEIN KINASES

CROSS REFERENCE TO RELATED APPLICATIONS

This present application claims the benefit, under 35 U.S.C. §119, to U.S. Provisional Application No. 60/505,634 filed Sep. 24, 2003, the entire disclosure of which is incorporated herein by reference.

TECHNICAL FIELD OF THE INVENTION

The present invention relates to compounds useful as inhibitors of protein kinases. The invention also provides processes for preparing the compounds of this invention, pharmaceutically acceptable compositions comprising the compounds of the invention, and methods of using the compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250–300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.* 1995, 9, 576–596; Knighton et al., *Science* 1991, 253, 407–414; Hiles et al., *Cell* 1992, 70, 419–429; Kunz et al., *Cell* 1993, 73, 585–596; Garcia-Bustos et al., *EMBO J.* 1994, 13, 2352–2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, cancer and other proliferative disorders. Accordingly, there has been a substantial effort in medicinal chemistry to find protein kinase inhibitors that are effective as therapeutic agents.

The c-Met proto-oncogene encodes the c-Met receptor tyrosine kinase. The c-Met receptor is a 190 kDa glycosylated dimeric complex composed of a 50 kDa alpha chain disulfide-linked to a 145 kDa beta chain. The alpha chain is found extracellularly while the beta chain contains extracellular transmembrane and cytosolic domains. c-Met is synthesized as a precursor and is proteolytically cleaved to yield mature alpha and beta subunits. It displays structural similarities to semaphorins and plexins, a ligand-receptor family that is involved in cell-cell interaction. The ligand for c-Met is hepatocyte growth factor (HGF), a member of the scatter factor family and has some homology to plasminogen [Longati, P. et al., *Curr. Drug Targets* 2001, 2, 41–55); Trusolino, L. and Comoglio, P. *Nature Rev. Cancer* 2002, 2, 289–300].

c-Met functions in tumorigenesis and tumor metastasis. Chromosomal rearrangements forming Tpr-met fusions in an osteoclast cell line resulted in constitutively active c-Met receptors and transformation (Cooper, C. S. et al., *Nature* 1984, 311, 29–33). c-Met mutants exhibiting enhanced kinase activity have been identified in both hereditary and sporadic forms of papillary renal carcinoma (Schmidt, L. et al., *Nat. Genet.* 1997, 16, 68–73; Jeffers, M. et al., *Proc. Nat. Acad. Sci.* 1997, 94, 11445–11500). Expression of c-Met along with its ligand HGF is transforming, tumorigenic, and metastatic (Jeffers, M. et al., *Oncogene* 1996, 13, 853–856; Michieli, P. et al., *Oncogene* 1999, 18, 5221–5231). HGF/Met has been shown to inhibit anoikis, suspension-induced programmed cell death (apoptosis), in head and neck squamous cell carcinoma cells. Anoikis resistance or anchorage-independent survival is a hallmark of oncogenic transformation of epithelial cells (Zeng, Q. et al., *J. Biol. Chem.* 2002, 277, 25203–25208).

c-Met is overexpressed in a significant percentage of human cancers and is amplified during the transition between primary tumors and metastasis. To investigate whether this oncogene is directly responsible for the acquisition of the metastatic phenotype, Giordano et al. exploited a single-hit oncogenic version of c-Met that was able to transform and to confer invasive and metastatic properties to nontumorigenic cells, both in vitro and in nude mice. They found a point mutation in the signal transducer docking site of c-Met that increased the transforming ability of the oncogene, but abolished its metastatic potential. They concluded that the metastatic potential of the c-Met oncogene relies on the properties of its multifunctional docking site, and that a single point mutation affecting signal transduction can dissociate neoplastic transformation from metastasis. Giordano, S., et al, *Proc. Nat. Acad. Sci.* 94: 13868–13872, 1997.

c-Met is implicated in various cancers. One cancer type in which c-Met is implicated is gastric adenocarcinoma. The American Cancer Society has projected that in 2004, 22,710 people will be diagnosed with gastric cancer and 11,780 will die of the disease in the United States. The five-year survival rate for patients who present with late stage disease involving the proximal region of the stomach is only 10–15%.

c-Met is amplified in 19–39% of gastric adeno-carcinomas, with highest amplification rates seen in diffuse type gastric adenocarcinoma. Tahara, E. (2004) Genetic Pathways of Two Tpes of Gastric Cancer. *IARC Sci Publ.* 2004, (157): 327–49. c-Met is also over-expressed in approximately 70% of gastric adenocarcinomas as examined by immunohistochemistry with over-expression correlating with tumor stage. Heideman D. A. et al., 2001, *J Pathol* 194: 428–435; Absence of tpr-met and expression of c-Met in human gastric mucosa and carcinoma; Amemiya, H. et al., 2002, c-Met Expression in Gastric Cancer with Liver Metastasis *Oncology* 63: 286–296. The potential for autocrine activation of c-Met exists in approximately 50% of patients as their tumors also express HGF[3].

c-Met is also implicated in renal cancer. It was found that the beta-subunit of the c-Met protooncogene product is the cell-surface receptor for hepatocyte growth factor. It was also identified that the hepatocyte growth factor receptor is the c-Met protooncogene product. Bottaro, D. P., et al, 1991, *Science* 251: 802–804.

c-Met is also implicated in small cell lung carcinoma. Small cell lung cancer is an aggressive disease that has a 5-year survival of 5–10% (mostly limited disease patients). In 2004, the number of new cases of lung cancer, which includes both small cell and non-small cell types, is 173,770 with 160,440 patients dying from the disease.

In 2003, small cell lung cancer made up approximately 16% of all lung cancer cases. Jemal A., et al., 2003, Cancer statistics, 2003. *CA Cancer J. Clin.*, 53: 5–26; Ma P. C., et al., 2003, c-MET mutational analysis in small cell lung cancer: novel juxtamembrane domain mutations regulating cytoskeletal functions. *Cancer Res.* 63: 6272–81. Both c-Met and c-Kit are co-expressed in the majority of small cell cancer cell lines and tumors and 30% of cell lines examined harbor mutations in c-Met. Rygaard K, et al., 1993, Expression of the proto-oncogenes c-Met and c-Kit and their ligands, hepatocyte growth factor/scatter factor and stem cell factor, in SCLC cell lines and xenografts. *Br J Cancer.* 67(1): 37–46. HGF is co-expressed in a small number of tumors.

The nexus between c-Met and colorectal cancer has also been established. Analysis of c-Met expression during colorectal cancer progression showed that 50% of the carcinoma specimens analyzed expressed 5–50-fold higher levels of c-Met mRNA transcripts and protein versus the adjacent normal colonic mucosa. In addition, when compared to the primary tumor, 70% of colorectal cancer liver metastasis showed c-Met over expression. See Long et al., 2003, Met Receptor Overexpression and Oncogenic Kiras Mutation Cooperate to Enhance Tumorigenicity of Colon Cancer Cells in Vivo. *Mol Cancer Res.* March; 1(5): 393–401; Fujisaki, et al., 1999, CD44 stimulation induces integrin-mediated adhesion of colon cancer cell lines to endothelial cells by up-regulation of integrins and c-Met and activation of integrins. *Cancer Res.* September 1;59 (17): 4427–34; Hiscox et al., Association of the HGF/SF receptor, c-Met, with the cell-surface adhesion molecule, E-cadherin, and catenins in human tumor cells. *Biochem Biophys Res Commun.* 1999, Aug. 2; 261(2): 406–11; Herynk et al., 2003, Activation of c-Met in colorectal carcinoma cells leads to constitutive association of tyrosine-phosphorylated beta-catenin. *Clin Exp Metastasis.* 20(4): 291–300; Wielenga et al., Expression of c-Met and heparan-sulfate proteoglycan forms of CD44 in colorectal cancer. *Am J Pathol.* 2000 November;157(5): 1563–73; Di Renzo et al., 1995, Overexpression and amplification of the Met/HGF receptor gene during the progression of colorectal cancer. *Clin. Cancer Res.*, 1: 147–154; and Mao, et al., 1997, Activation of c-Src by receptor tyrosine kinases in human colon cancer cells with high metastatic potential. *Oncogene,* 15:3083–3090.

The c-Met receptor tyrosine kinase ("RTK") is also implicated in glioblastoma. High-grade malignant gliomas are the most common cancers of the central nervous system., Despite treatment with surgical resection, radiation therapy, and chemotherapy, the mean overall survival is <1.5 years, and few patients survive for >3 years. A common reason for treatment failure is their innate resistance to radiation and chemotherapy.

Glioblastoma multiforme is the most common and most malignant glial neoplasm. Despite very aggressive treatment, these malignant gliomas are associated with an average life expectancy of only 9 months. The formation and malignant progression of human gliomas are complex processes and involve genetic mutations, chromosomal multiploidy, and aberrant epigenetic influences of multiple mitogens and angiogenic factors.

Human malignant gliomas frequently express both HGF and c-Met, which can establish an autocrine loop of biological significance. Glioma c-Met expression correlates with glioma grade, and an analysis of human tumor specimens showed that malignant gliomas have a 7-fold higher HGF content than low-grade gliomas.

On top of representing the most common form of primary central nervous system malignancy, gliomas are also among the tumors most tightly linked with HGF-cMet signaling abnormalities. Multiple studies have demonstrated that human gliomas frequently co-express HGF and c-Met and that high levels of expression are associated with malignant progression. HGF gene transfer to glioma cell lines enhances tumorigenicity, tumor growth, and tumor-associated angiogenesis. It has also been shown that blocking HGF-cMet signaling reverses these phenotypes in vivo. It was further shown that HGF-cMet is able to activate Akt and protect glioma cell lines from apoptotic death, both in vitro and in vivo. See Hirose et al., Clinical importance of c-Met protein expression in high-grade astrocytic tumors. *Neurol. Med.-Chir.* 38:851–859, 1998, Hirose et al., 1998, Immunohistochemical examination of cMet protein expression inastrocytic tumors. *Acta Neuropathol.* 95:345–351; Koochekpour et al., Met and hepatocyte growth factor expression in human gliomas. *Cancer Res.* 57:5391–5398; Laterra et al., HGF expression enhances human glioblastoma tumorigenicity and growth. *Biochem. Biophys. Res. Commun.* 235:743–747; Moriyama et al., 1995, Concomitant expression of hepatocyte growth factor, HGF activator and cMet genes in human glioma cells in vitro. *FEBs Lett.* 372:78–82; Nabeshima et al., Expression of cMet correlates with grade of malignancy in human astrocytic tumors: an immunohistochemical study. *Histopathology* 31:436–443, 1997, Shiota et al., Coexpression of hepatocyte growth factor and its receptor (cMet) in HGL4 glioblastoma cells. *Lab. Investig.* 53:511–516, 1996, Welch et al., Hepatocyte growth factor and receptor (cMet) in normal and malignant astrocytic cells. *Anticancer Res.* 19:1635–1640, 1999, Bowers et al., 2000, HGF protects against cytoxic death in human glioblastoma via PI3-K and Akt-dependent pathways. *Cancer Res.* 60:4277–4283.

It was shown that the effect of NK4 (HGF antagonist), on HGF-promoted growth of a human breast cancer resulted in the reduction of tumor invasiveness and motility, weight and volume. Furthermore, in the in-vitro invasion assay and migration assay, both HGF and human fibroblasts, which secrete bioactive HGF, increased the invasiveness and migration of the breast cancer cells (MDA MB 231). See Growth and angiogenesis of human breast cancer in a nude mouse tumor model is reduced by NK4, the HGF antagonist. *Carcinogenesis, May* 9, 2003. Furthermore, transgenic mice harboring mutationally activated c-Met developed metastic mammary carcinoma. These same activating mutants were able to establish tumors in nude mouse NIH 3T3 xenografts (*PNAS*, Vol 95, pp 14417–14422, November 1998).

Transgenic mice that overexpressed c-Met in hepatocytes developed heptocellular carcinoma (HCC), one of the human tumors in which c-Met has been implicated previously. Inactivation of the transgene led to regression of even highly advanced tumors, apparently mediated by apoptosis and cessation of cellular proliferation. Numerous cells were proliferating in the liver tumors that were elicited by c-Met. Removal of the stimulus from the transgenic hMet led to prompt cessation of cellular proliferation even in the cells of advanced malignancies (*The Journal of Cell Biology*, Vol. 153, 2001, p. 1023–1033).

HGF/Met signaling is involved in cell adhesion and motility in normal cells and plays a major role in the invasive growth that is found in most tissues, including cartilage, bone, blood vessels, and neurons (reviewed in Comoglio, P. M. and Trusolino, L. *J. Clin. Invest.* 2002, 109, 857–862). Dysfunctional activation or increased numbers of c-Met is likely to contribute to the aberrant cell-cell interactions that lead to migration, proliferation, and survival of cells that is characteristic of tumor metastasis. Activation of c-Met induces and sustains a variety of tumors [Wang, R. et al., *J. Cell. Biol.* 2001, 153, 1023–1034; Liang, T. J. et al., *J. Clin. Invest.* 1996, 97, 2872–2877; Jeffers, M. et al., *Proc. Nat. Acad. Sci.* 1998, 95, 14417–14422] while loss of c-Met inhibits growth and invasiveness of tumor cells [Jiang, W. G. et al., *Clin. Cancer Res.* 2001, 7, 2555–2562; Abounader, R. et al., *FASEB J.* 2002 16, 108–110]. Increased expression of Met/HGF is seen in many metastatic tumors including colon (Fazekas, K. et al., *Clin. Exp. Metastasis* 2000, 18, 639–649), breast (Elliott, B. E. et al., 2002, *Can. J. Physiol. Pharmacol.* 80, 91–102), prostate (Knudsen, B. S. et al., *Urology* 2002, 60, 1113–1117), lung (Siegfried, J. M. et al., *Ann. Thorac. Surg.* 1998, 66, 1915–1918), and gastric (Amemiya, H. et al., *Oncology* 2002, 63, 286–296).

Further demonstration of the role c-Met plays in metastasis was shown by Giordano, et al. (2002) who presented evidence for cross-talk between the semaphorin 4D (SEMA4D; 601866) receptor, plexin B1 (PLXNB1; 601053), and c-Met during invasive growth in epithelial cells. Binding of SEMA4D to PLXNB1 stimulated tyrosine kinase activity of MET, resulting in tyrosine phosphorylation of both receptors. This effect was not found in cells lacking c-Met expression. Giordano, S., et al: 2002, The Semaphorin 4D receptor controls invasive growth by coupling with Met. *Nature Cell Biol.* 4: 720–724.

HGF-c-Met signaling has also been associated with increased risk of atherosclerosis (Yamamoto, Y. et al., *J. Hypertens.* 2001, 19, 1975–1979; Morishita, R. et al., *Endocr. J.* 2002, 49, 273–284) and increased fibrosis of the lung (Crestani, B. et al., *Lab. Invest.* 2002, 82, 1015–1022).

The Janus kinases (JAK) are a family of tyrosine kinases consisting of JAK1, JAK2, JAK3 and TYK2. The JAKs play a critical role in cytokine signaling. The downstream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. The pharmaceutical intervention in the JAK/STAT pathway has been reviewed [*Frank Mol. Med.* 5: 432–456 1999 & Seidel, et al, *Oncogene* 19: 2645–2656 2000].

JAK1, JAK2, and TYK2 are ubiquitously expressed, while JAK3 is predominantly expressed in hematopoietic cells. JAK3 binds exclusively to the common cytokine receptor gamma chain (gc) and is activated by IL-2, IL-4, IL-7, IL-9, and IL-15. The proliferation and survival of murine mast cells induced by IL-4 and IL?9 have, in fact, been shown to be dependent on JAK3- and gc-signaling [Suzuki et al, 2000, *Blood* 96: 2172–2180].

Cross-linking of the high-affinity immunoglobulin (Ig) E receptors of sensitized mast cells leads to a release of proinflammatory mediators, including a number of vasoactive cytokines resulting in acute allergic, or immediate (type I) hypersensitivity reactions [Gordon et al, 1990; *Nature* 346: 274–276 & Galli, 1993, *N. Engl. J. Med.*, 328: 257–265]. A crucial role for JAK3 in IgE receptor-mediated mast cell responses in vitro and in vivo has been established [Malaviya, et al, 1999, *Biochem. Biophys. Res. Commun.* 257: 807–813]. In addition, the prevention of type I hypersensitivity reactions, including anaphylaxis, mediated by mast cell-activation through inhibition of JAK3 has also been reported [Malaviya et al, 1999; *J. Biol. Chem.* 274: 27028–27038]. Targeting mast cells with JAK3 inhibitors modulated mast cell degranulation in vitro and prevented IgE receptor/antigen-mediated anaphylactic reactions in vivo.

A recent study described the successful targeting of JAK3 for immune suppression and allograft acceptance. The study demonstrated a dose-dependent survival of Buffalo heart allograft in Wistar Furth recipients upon administration of inhibitors of JAK3 indicating the possibility of regulating unwanted immune responses in graft versus host disease [Kirken, transpl. proc. 33: 3268–3270 2001].

IL-4-mediated STAT-phosphorylation has been implicated as the mechanism involved in early and late stages of rheumatoid arthritis (RA). Up-regulation of proinflammatory cytokines in RA synovium and synovial fluid is a characteristic of the disease. It has been demonstrated that IL-4-mediated activation of IL-4/STAT pathway is mediated through the Janus Kinases (JAK 1 & 3) and that IL-4-associated JAK kinases are expressed in the RA synovium [Muller-Ladner, et al, 2000, *J. Immunol.* 164: 3894–3901].

Familial amyotrophic lateral sclerosis (FALS) is a fatal neurodegenerative disorder affecting about 10% of ALS patients. The survival rates of FALS mice were increased upon treatment with a JAK3 specific inhibitor. This confirmed that JAK3 plays a role in FALS [Trieu, et al, 2000, *Biochem. Biophys. Res. Commun.* 267: 22–25].

Signal transducer and activator of transcription (STAT) proteins are activated by, among others, the JAK family kinases. Results form a recent study suggested the possibility of intervention in the JAK/STAT signaling pathway by targeting JAK family kinases with specific inhibitors for the treatment of leukemia [Sudbeck, et al, 1999, *Clin. Cancer Res.* 5: 1569–1582]. JAK3 specific compounds were shown to inhibit the clonogenic growth of JAK3-expressing cell lines DAUDI, RAMOS, LC1; 19, NALM-6, MOLT-3 and HL-60.

In animal models, TEL/JAK2 fusion proteins have induced myeloproliferative disorders and in hematopoietic cell lines, introduction of TEL/JAK2 resulted in activation of STAT1, STAT3, STAT5, and cytokine-independent growth [Schwaller, et al, 1998, *EMBO J.* 17: 5321–5333].

Inhibition of JAK 3 and TYK 2 abrogated tyrosine phosphorylation of STAT3, and inhibited cell growth of mycosis fungoides, a form of cutaneous T cell lymphoma.

These results implicated JAK family kinases in the constitutively activated JAK/STAT pathway that is present in mycosis fungoides [Nielsen, et al, Proc. Nat. Acad. Sci. U.S.A. 94: 6764–6769 (1997)]. Similarly, STAT3, STAT5, JAK1 and JAK2 were demonstrated to be constitutively activated in mouse T cell lymphoma characterized initially by LCK over-expression, thus further implicating the JAK/STAT pathway in abnormal cell growth [Yu, et al, 1997, *J. Immunol.* 159: 5206–5210]. In addition, IL-6-mediated STAT3 activation was blocked by an inhibitor of JAK, leading to sensitization of myeloma cells to apoptosis [Catlett-Falcone, et al, 1999; *Immunity* 10: 105–115].

Tyrosine kinases are a class of enzymes that mediate intracellular signal transduction pathways. Abnormal activity of these kinases has been shown to contribute to cell proliferation, carcinogenesis and cell differentiation. Thus, agents that modulate the activity of tyrosine kinases are useful for preventing and treating proliferative diseases associated with these enzymes.

KDR is a tyrosine kinase receptor that also binds VEGF (vascular endothelial growth factor) Neufeld et al., 1999, *FASEB J.*, 13, 9. The binding of VEGF to the KDR receptor leads to angiogenesis, which is the sprouting of capillaries from preexisting blood vessels. High levels of VEGF are found in various cancers causing tumor angiogenesis and permitting the rapid growth of cancerous cells. Therefore, suppressing VEGF activity is a way to inhibit tumor growth, and it has been shown that this can be achieved by inhibiting KDR receptor tyrosine kinase. For example, SU5416 is a selective inhibitor of the tyrosine kinase and was reported to also suppress tumor vascularization and the growth of multiple tumors. Fong et al., 1999, *Cancer Res.* 59, 99. Other inhibitors of KDR tyrosine kinase for the treatment of cancer have also been reported (WO 98/54093, WO 99/16755, WO 00/12089).

Examples of cancers that may be treated by such inhibitors include brain cancer, genitourinary tract cancer, lymphatic system cancer, gastric cancer, cancer of the larynx, lung cancer, pancreatic cancer, breast cancer, Kaposi's sarcoma, and leukemia. Other diseases and conditions associated with abnormal tyrosine kinase activity include vascular disease, autoimmune diseases, ocular conditions, and inflammatory diseases.

As a result of the biological importance of protein kinases, there is current interest in therapeutically effective protein kinase inhibitors. Accordingly, there is still a great need to develop inhibitors of protein kinases that are useful in treating various diseases or conditions associated with protein kinase activation. In particular, it would be desirable to develop compounds that are useful as inhibitors of c-Met, JAK, and KDR particularly given the inadequate treatments currently available for the majority of the disorders implicated in their activation.

SUMMARY OF THE INVENTION

It has now been found that compounds of this invention, and pharmaceutically acceptable compositions thereof, are effective as inhibitors of protein kinases. In certain embodiments, these compounds are effective as inhibitors of c-Met, JAK, and KDR protein kinases, either alone or in combination. These compounds have the general formula I:

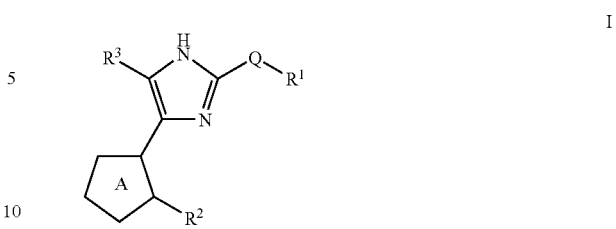

or a pharmaceutically acceptable salt thereof, wherein Ring A, $R^1$, $R^2$, $R^3$, and Q are as defined below.

These compounds and pharmaceutically acceptable compositions thereof are useful for treating or preventing a variety of diseases, disorders or conditions, including, but not limited to, cancer and other proliferative disorders.

The compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

I. General Description of Compounds of the Invention

The present invention relates to a compound of formula I:

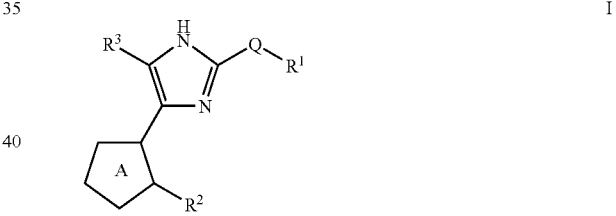

or a pharmaceutically acceptable salt thereof, wherein:

Q is a $C_{1-6}$ alkylidene chain wherein one methylene unit of Q is replaced by —C(O)N(R)—, —C(O)—, —C(O)O—, —N(R)—, —O—, —S—, —SO$_2$—, or —SO$_2$N(R)—;

each R is independently hydrogen or an optionally substituted $C_{1-6}$ aliphatic group, wherein:

two R groups on the same nitrogen atom are optionally taken together with said nitrogen atom to form an optionally substituted 3–7 membered saturated, partially unsaturated, or fully unsaturated ring having 1–3 heteroatoms independently selected from nitrogen, oxygen, or sulfur;

$R^1$ is H, —N(R)$_2$, or an optionally substituted ring selected from a 3–7 membered saturated or partially unsaturated ring having 0–3 heteroatoms independently selected from nitrogen, oxygen, or sulfur; a 5–6 membered aryl ring having 0–4 heteroatoms independently selected from nitrogen, oxygen, or sulfur; or an 8–10 membered bicyclic partially unsaturated or aryl ring having 0–4 heteroatoms independently selected from nitrogen, oxygen, or sulfur;

R² is an optionally substituted 6-membered aryl ring having 0–3 nitrogens;
R³ is R, CN, NO₂, halogen, N(R)₂, OR, or SR; and
Ring A is an optionally substituted ring selected from:
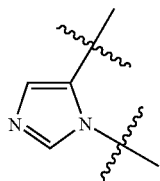
a
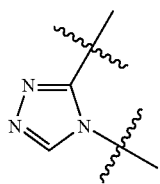
b
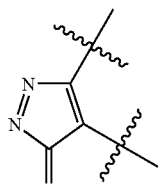
c
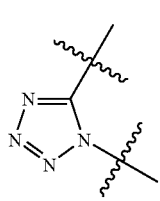
d
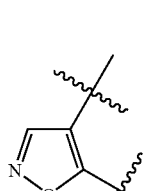
e
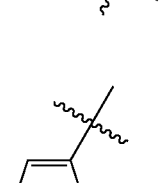
f
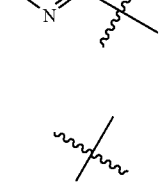
g
-continued
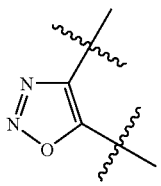
h
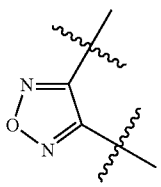
i
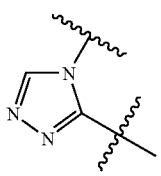
j
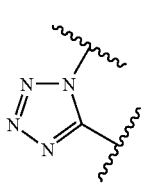
k
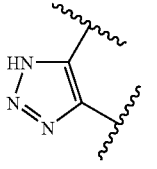
l
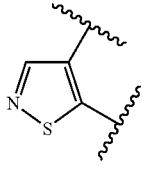
m
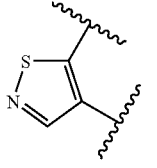
n
o
or

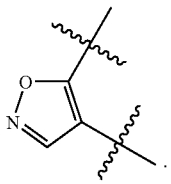

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, a number of atoms specified as a range includes any integer therein. For example, a group having from 1–4 atoms could have 1, 2, 3, or 4 atoms.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1–20 aliphatic carbon atoms. In some embodiments, aliphatic groups contain 1–10 aliphatic carbon atoms. In other embodiments, aliphatic groups contain 1–8 aliphatic carbon atoms. In still other embodiments, aliphatic groups contain 1–6 aliphatic carbon atoms, and in yet other embodiments aliphatic groups contain 1–4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3–7 members. Examples of aliphatic groups include, but are not limited to, linear or branched, alkyl, alkenyl, alkynyl, cycloalkyl, cycloalkenyl, cycloalkynyl groups and hybrids thereof such as (cycloalkyl)alkyl, (cycloalkenyl)alkyl or (cycloalkyl)alkenyl.

The term "heterocycle", "heterocyclyl", "heterocycloaliphatic", or "heterocyclic" as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members. Examples of heterocyclic rings include, but are not limited to, 3-1H-benzimidazol-2-one, 3-(1-alkyl)benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined herein below. Examples of aryl compounds include, but are not limited to, phenyl, naphthyl, and any of the heteroaryl groups listed below.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Examples of heteroaryl groups include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; $-R^\circ$; $-OR^\circ$; $-SR^\circ$; 1,2-methylenedioxy; 1,2-ethylenedioxy; phenyl (Ph) optionally substituted with $R^\circ$; $-O(Ph)$ optionally substituted with $R^\circ$; $-(CH_2)_{1-2}(Ph)$, optionally substituted with $R^\circ$; $-CH=CH(Ph)$, optionally substituted with $R^\circ$; $-NO_2$; $-CN$; $-N(R^\circ)_2$; $-NR^\circ C(O)R^\circ$; $-NR^\circ C(S)R^\circ$; $-NR^\circ C(O)N(R^\circ)_2$; $-NR^\circ C(S)N(R^\circ)_2$; $-NR^\circ CO_2R^\circ$; $-NR^\circ NR^\circ C(O)R^\circ$; $-NR^\circ NR^\circ C(O)N(R^\circ)_2$; $-NR^\circ NR^\circ CO_2R^\circ$; $-C(O)C(O)R^\circ$; $-C(O)CH_2C(O)R^\circ$; $-CO_2R^\circ$; $-C(O)R^\circ$; $-C(S)R^\circ$; $-C(O)N(R^\circ)_2$; $-C(S)N(R^\circ)_2$; $-OC(O)N(R^\circ)_2$; $-OC(O)R^\circ$; $-C(O)N(OR^\circ)R^\circ$; $-C(NOR^\circ)R^\circ$; $-S(O)_2R^\circ$; $-S(O)_3R^\circ$; $-SO_2N(R^\circ)_2$; $-S(O)R^\circ$; $-NR^\circ SO_2N(R^\circ)_2$; $-NR^\circ SO_2R^\circ$; $-N(OR^\circ)R^\circ$; $-C(=NH)-N(R^\circ)_2$; or $-(CH_2)_{0-2}NHC(O)R^\circ$ wherein each independent occurrence of $R^\circ$ is selected from hydrogen, optionally substituted $C_{1-6}$ aliphatic, an unsubstituted 5–6 membered heteroaryl or heterocyclic ring, phenyl, $-O(Ph)$, or $-CH_2(Ph)$, or, notwithstanding the definition above, two independent occurrences of $R^\circ$, on the same substituent or different substituents, taken together with the atom(s) to which each $R^\circ$ group is bound, form a 5–8-membered heterocyclyl, aryl, or heteroaryl ring or a 3–8-membered cycloalkyl ring having 0–3 heteroatoms independently selected from nitrogen, oxygen, or sulfur. Optional substituents on the aliphatic group of $R^\circ$ are selected from $NH_2$, $NH(C_{1-4}aliphatic)$, $N(C_{1-4}aliphatic)_2$, halogen, $C_{1-4}aliphatic$, OH, $O(C_{1-4}aliphatic)$, $NO_2$, CN, $CO_2H$, $CO_2(C_{1-4}aliphatic)$, $O(haloC_{1-4}$ aliphatic), or $haloC_{1-4}aliphatic$, wherein each of the foregoing $C_{1-4}$ aliphatic groups of $R^\circ$ is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: $=O$, $=S$, $=NNHR^*$, $=NN(R^*)_2$, $=NNHC(O)R^*$, $=NNHCO_2(alkyl)$, $=NNHSO_2(alkyl)$, or $=NR^*$, where each $R^*$ is independently selected from hydrogen or an optionally substituted $C_{1-6}$ aliphatic. Optional substituents on the aliphatic group of $R^*$ are selected from $NH_2$, $NH(C_{1-4}$ aliphatic), $N(C_{1-4}$ aliphatic$)_2$, halogen, $C_{1-4}$ aliphatic, OH, $O(C_{1-4}$ aliphatic), $NO_2$, CN, $CO_2H$, $CO_2(C_{1-4}$ aliphatic), $O(halo$ $C_{1-4}$ aliphatic), or halo ($C_{1-4}$ aliphatic), wherein each of the foregoing $C_{1-4}$aliphatic groups of $R^*$ is unsubstituted.

Optional substituents on the nitrogen of a non-aromatic heterocyclic ring are selected from $-R^+$, $-N(R^+)_2$, $-C(O)R^+$, $-CO_2R^+$, $-C(O)C(O)R^+$, $-C(O)CH_2C(O)R^+$, $-SO_2R^+$, $-SO_2N(R^+)_2$, $-C(=S)N(R^+)_2$, $-C(=NH)-N(R^+)_2$, or $-NR^+SO_2R^+$; wherein $R^+$ is hydrogen, an optionally substituted $C_{1-6}$ aliphatic, optionally substituted phenyl, optionally substituted $-O(Ph)$, optionally substituted $-CH_2(Ph)$, optionally substituted $-(CH_2)_{1-2}(Ph)$; optionally substituted $-CH=CH(Ph)$; or an unsubstituted 5–6 membered heteroaryl or heterocyclic ring having one to four heteroatoms independently selected from oxygen, nitrogen, or sulfur, or, notwithstanding the definition above, two independent occurrences of $R^+$, on the same substituent or different substituents, taken together with the atom(s) to which each $R^+$ group is bound, form a 5–8-membered heterocyclyl, aryl, or heteroaryl ring or a 3–8-membered cycloalkyl ring having 0–3 heteroatoms independently selected from nitrogen, oxygen, or sulfur. Optional substituents on the aliphatic group or the phenyl ring of $R^+$ are selected from $NH_2$, $NH(C_{1-4}$ aliphatic), $N(C_{1-4}$ aliphatic$)_2$, halogen, $C_{1-4}$ aliphatic, OH, $O(C_{1-4}$ aliphatic), $NO_2$, CN, $CO_2H$, $CO_2(C_{1-4}$ aliphatic), $O(halo$ $C_{1-4}$ aliphatic), or halo ($C_{1-4}$ aliphatic), wherein each of the foregoing $C_{1-4}$aliphatic groups of $R^+$ is unsubstituted.

The term "alkylidene chain" refers to a straight or branched carbon chain that may be fully saturated or have one or more units of unsaturation and has two points of attachment to the rest of the molecule. Alkylidene, therefore, includes aliphatic groups (alkyl, alkenyl, or alkynyl) that have two points of attachment to the rest of the molecule.

As detailed above, in some embodiments, two independent occurrences of $R^\circ$ (or $R^+$, or any other variable similarly defined herein), are taken together with the atom(s) to which each variable is bound to form a 5–8-membered heterocyclyl, aryl, or heteroaryl ring or a 3–8-membered cycloalkyl ring having 0–3 heteroatoms independently selected from nitrogen, oxygen, or sulfur. Exemplary rings that are formed when two independent occurrences of $R^\circ$ (or $R^+$, or any other variable similarly defined herein) are taken together with the atom(s) to which each variable is bound include, but are not limited to the following: a) two independent occurrences of $R^\circ$ (or $R^+$, or any other variable similarly defined herein) that are bound to the same atom and are taken together with that atom to form a ring, for example, $N(R^\circ)_2$, where both occurrences of $R^\circ$ are taken together with the nitrogen atom to form a piperidin-1-yl, piperazin-1-yl, or morpholin-4-yl group; and b) two independent occurrences of $R^\circ$ (or $R^+$, or any other variable similarly defined herein) that are bound to different atoms and are taken together with both of those atoms to form a ring, for example where a phenyl group is substituted with two occurrences of $OR^\circ$

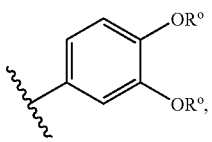

these two occurrences of R° are taken together with the oxygen atoms to which they are bound to form a fused 6-membered oxygen containing ring:

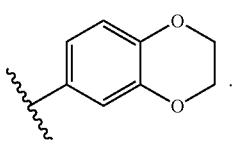

It will be appreciated that a variety of other rings can be formed when two independent occurrences of R° (or R+, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

3. Description of Exemplary Compounds

According to one embodiment, the present invention relates to a compound of formula I wherein Q is a $C_{1-6}$ alkylidene chain wherein one methylene unit of Q is replaced by —C(O)— or —C(O)N(R)—.

According to another embodiment, Q is a $C_{1-6}$ alkylidene chain wherein the methylene unit bonded to the imidazole core is replaced by —C(O)— or by —C(O)N(R)—.

According to another embodiment, Q is a $C_1$ alkylidene chain wherein the methylene unit is replaced by —C(O), (i.e., Q is C(O)).

According to another embodiment, Q is a $C_1$ alkylidene chain wherein the methylene unit is replaced by —C(O)N(R)— (i.e., Q is —C(O)N(R)—).

Another aspect of the present invention relates to a compound of formula I wherein $R^1$ is an optionally substituted ring selected from a 3–7 membered saturated or partially unsaturated ring having 0–3 heteroatoms independently selected from nitrogen, oxygen, or sulfur, a 5–6 membered aryl ring having 0–4 heteroatoms independently selected from nitrogen, oxygen, or sulfur, or an 8–10 membered bicyclic partially unsaturated or aryl ring having 0–4 heteroatoms independently selected from nitrogen, oxygen, or sulfur.

According to another embodiment, $R^1$ is a 4–6 membered unsaturated ring having 0–3 heteroatoms independently selected from nitrogen, oxygen, or sulfur. Such rings include cyclopentenyl and cyclohexenyl.

According to another embodiment, $R^1$ is a 4–6 membered saturated ring having 0–3 heteroatoms independently selected from nitrogen, oxygen, or sulfur. Such rings include cyclopentyl, cyclohexyl, tetrahydrofuranyl, pyrrolidin-1-yl, morpholin-4-yl, thiomorpholin-4-yl, piperidin-1-yl, and azetidin-1-yl.

According to another embodiment, $R^1$ is a 5–6 membered aryl ring having 0–4 heteroatoms independently selected from nitrogen, oxygen, or sulfur, or an 8–10 membered bicyclic partially unsaturated or aryl ring having 0–4 heteroatoms independently selected from nitrogen, oxygen, or sulfur.

Yet another aspect of the present invention relates to a compound of formula I wherein $R^2$ is an optionally substituted 6-membered aryl ring having 0–3 nitrogens.

According to another embodiment, $R^2$ is an optionally substituted phenyl ring. Examples of substituents on the $R^2$ phenyl ring, when present, include chloro and fluoro.

According to another embodiment, $R^2$ is an optionally substituted heteroaryl ring. Such rings include pyridyl and pyrimidinyl rings.

Another embodiment of the present invention relates to a compound of formula I wherein Ring A is an optionally substituted ring selected from isoxazolyl, imidazolyl, triazolyl, or tetrazolyl.

Yet another embodiment relates to a compound of formula I wherein Ring A is selected from the following rings:

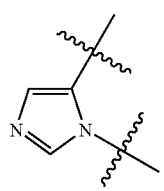

a

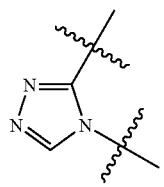

b

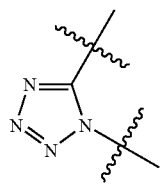

d

-continued

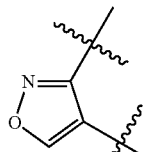

or

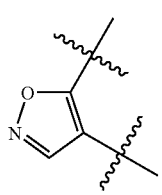

According to another embodiment, Ring A is isoxazolyl.
According to yet another embodiment, Ring A is selected from:

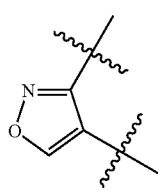

or

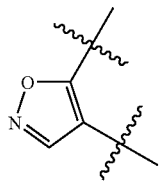

According to one embodiment, the present invention relates to a compound of formula I wherein Ring A is unsubstituted.

According to another embodiment, the present invention relates to a compound of formula I wherein Ring A is optionally substituted with oxo, —OH, —NH$_2$, or —CH$_3$.

It should be understood that any embodiment herein may be combined with any other embodiment. In certain embodiments, R$^1$, R$^2$, R$^3$, Q, and A are as depicted in Examples I-1 to I-40. Exemplary structures of formula I are set forth in Table 1, below.

TABLE 1

Examples of Compounds of Formula I:

I-1

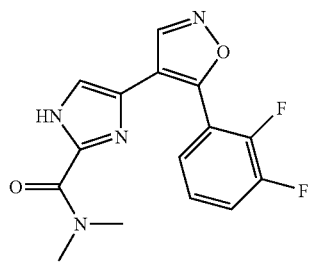

TABLE 1-continued

Examples of Compounds of Formula I:

I-2

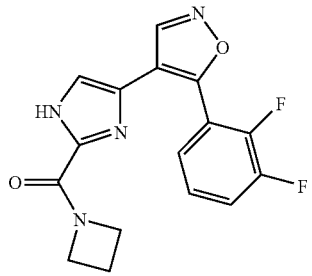

I-3

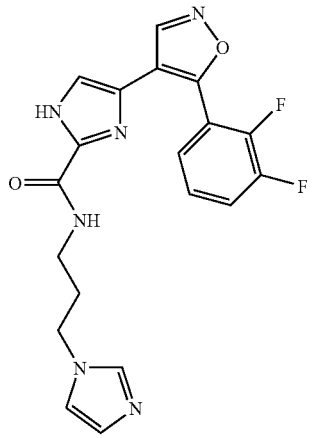

I-4

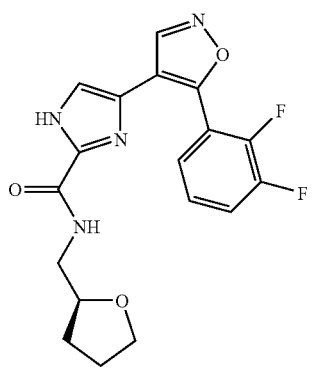

I-5

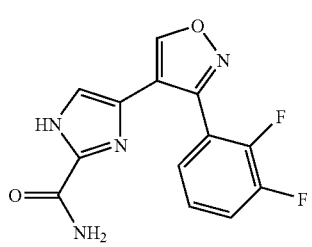

TABLE 1-continued
Examples of Compounds of Formula I:
I-6
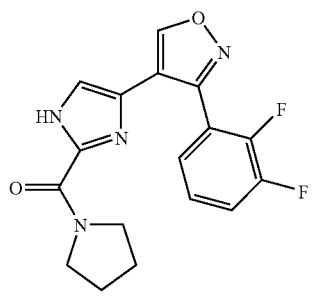
I-7
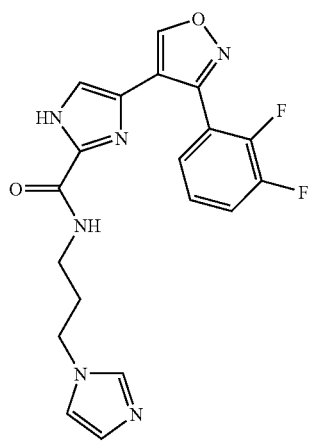
I-8
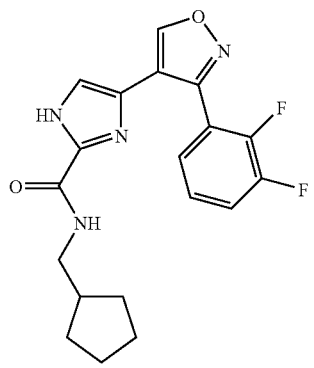
I-9
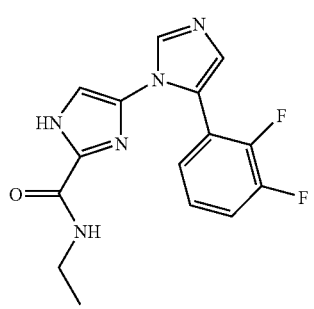
TABLE 1-continued
Examples of Compounds of Formula I:
I-10
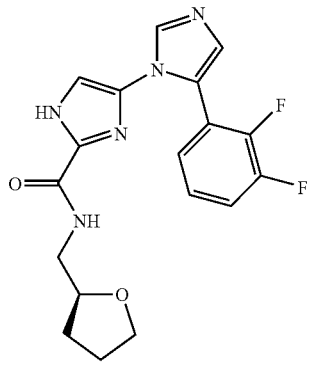
I-11
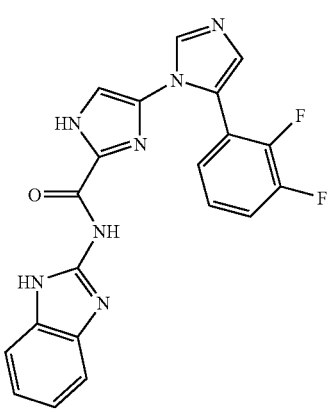
I-12
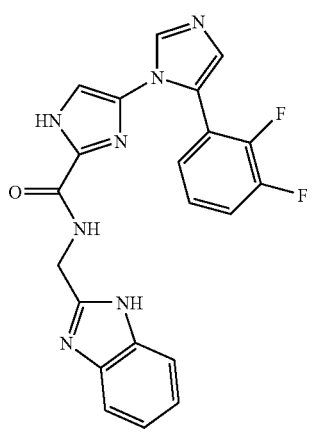
I-13
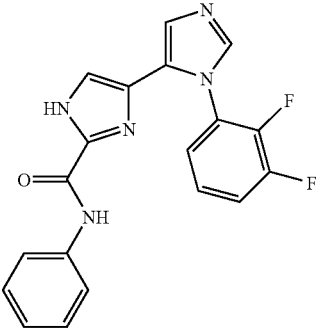

TABLE 1-continued
Examples of Compounds of Formula I:
I-14
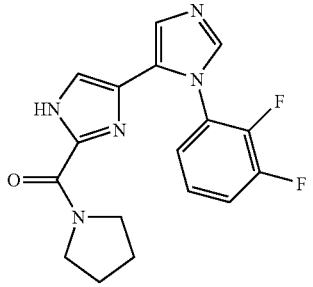
I-15
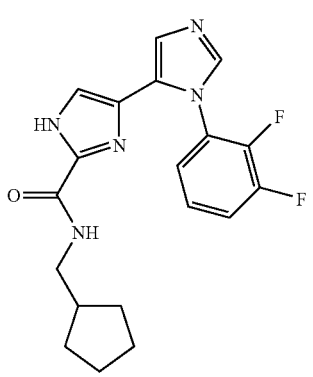
I-16
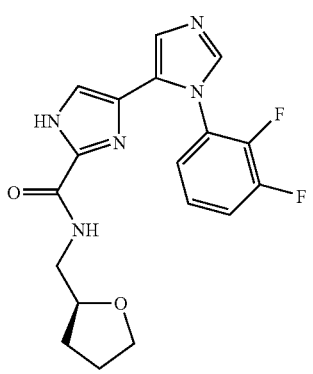
I-17
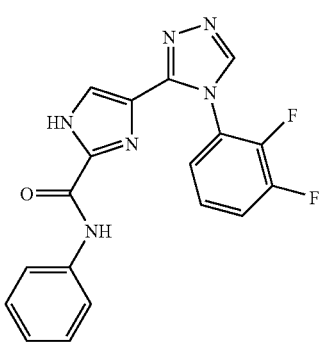
TABLE 1-continued
Examples of Compounds of Formula I:
I-18
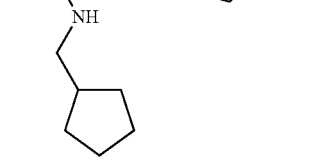
I-19
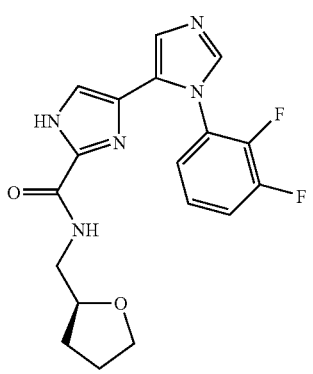
I-20
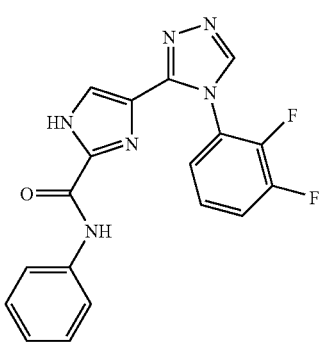
I-21
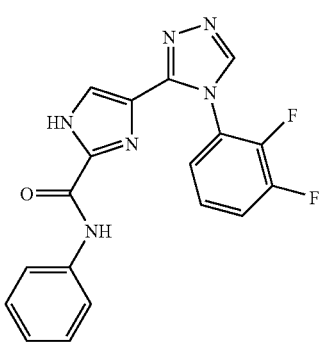

TABLE 1-continued
Examples of Compounds of Formula I:
I-22
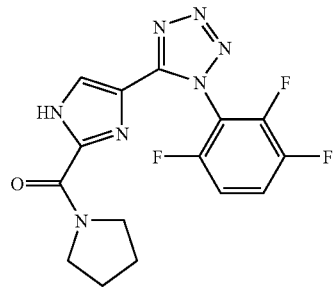
I-23
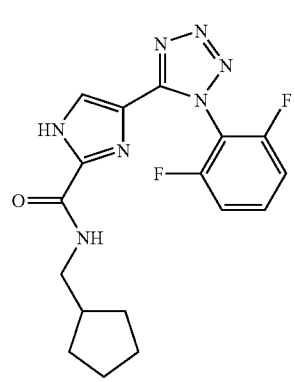
I-24
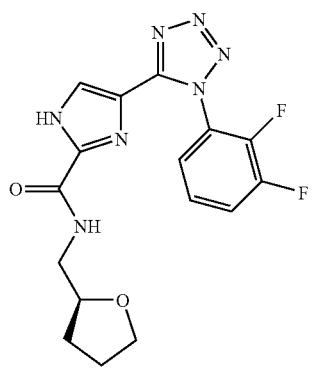
I-25
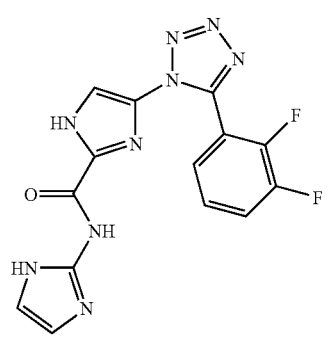
TABLE 1-continued
Examples of Compounds of Formula I:
I-26
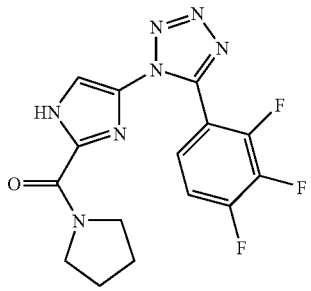
I-27
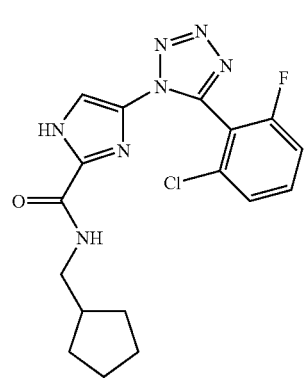
I-28
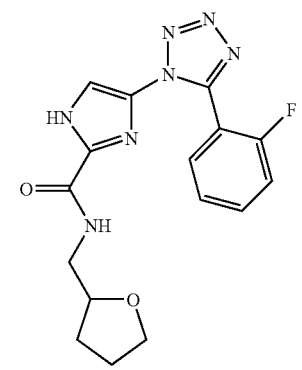
I-29
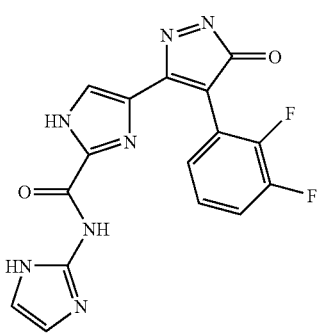

TABLE 1-continued
Examples of Compounds of Formula I:
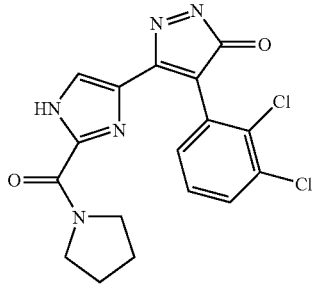
I-30
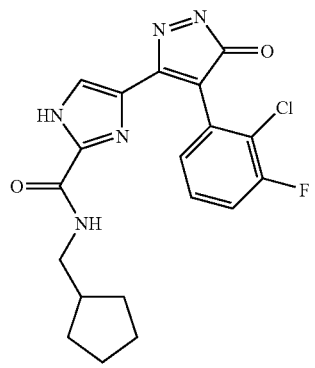
I-31
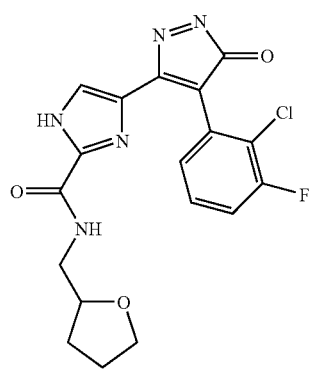
I-32
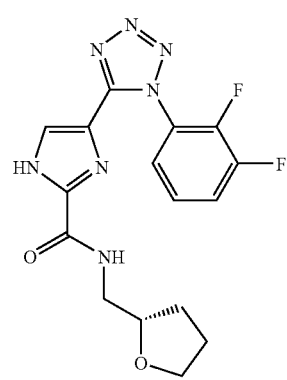
I-33
TABLE 1-continued
Examples of Compounds of Formula I:
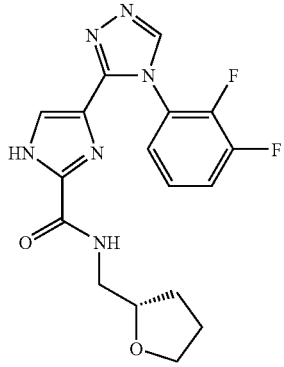
I-34
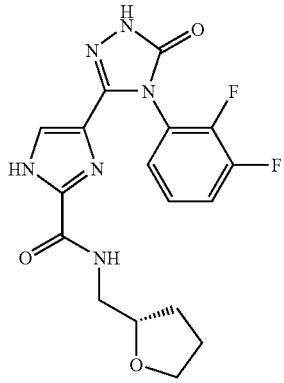
I-35
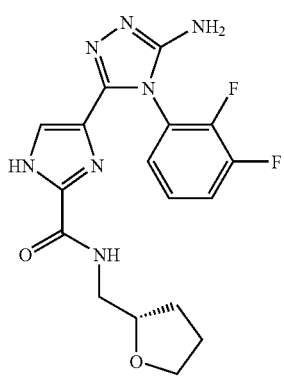
I-36
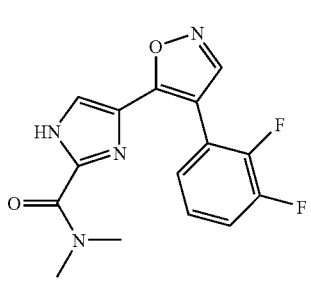
I-37

TABLE 1-continued

Examples of Compounds of Formula I:

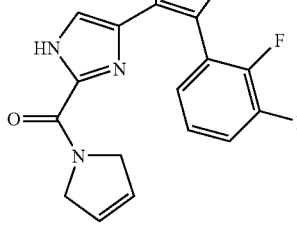

I-38

I-39

I-40

4. General Synthetic Methodology

The compounds of this invention may be prepared in general by methods known to those skilled in the art for analogous compounds, as illustrated by the general scheme below, and the preparative examples that follow.

Scheme I

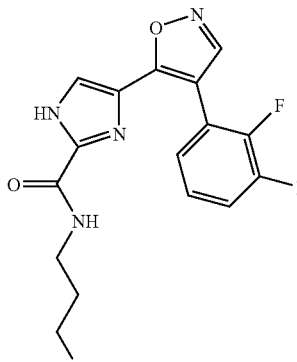

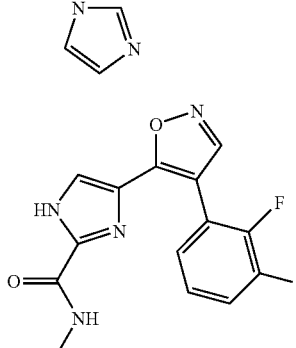

Reagents and conditions: (i). NaH, BnCl, THF, r.t.; (ii). a. LiN(TMS)$_2$, THF, -78° C. to 0° C.; b. R$^2$CO$_2$Me; c. 2N HCl; (iii). ClCOCCl$_3$, AlCl$_3$, DCM; (iv). R$^1$NH$_2$, CH$_3$CN, r.t.; (v). Pd/C, MeOH, HCOOH; vi: a. Bredreck's reagent, THF, 60° C.; b. H$_2$NOH HCl, EtOH, reflux.

Scheme I above shows a general synthetic route for preparing compounds of the present invention when Ring A is isoxazolyl.

Scheme II

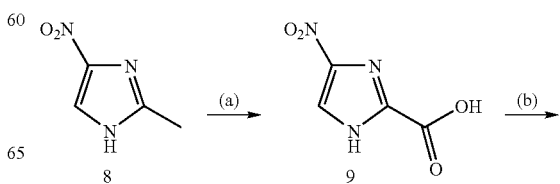

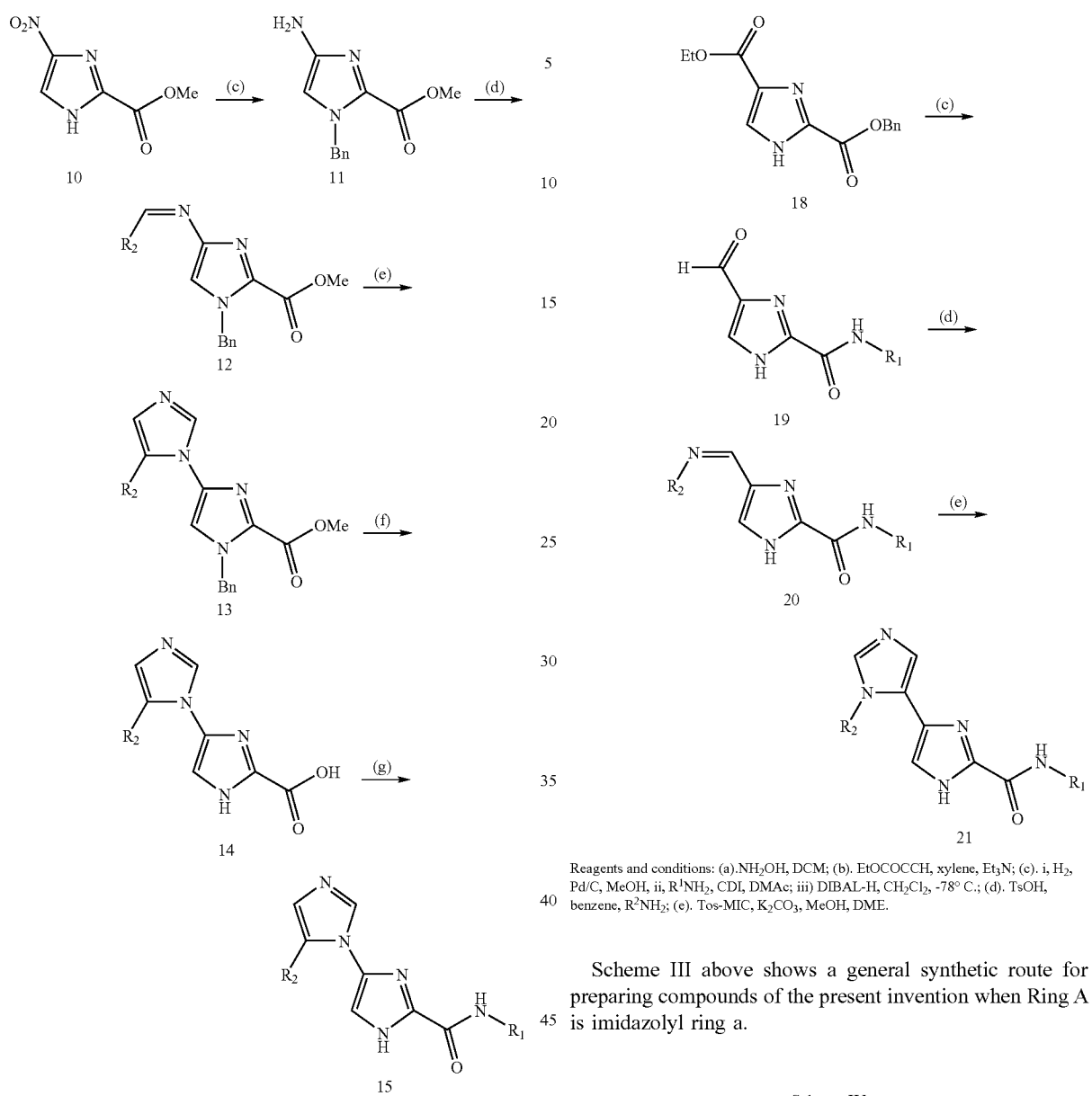

Reagents and conditions: (a). KMnO₄; (b). MeOH, HCl; (c). i, NaH, BnCl, THF; ii, Fe, HCl; (d). TsOH, benzene, R²C(O)H; (e). Tos-MIC, K₂CO₃, MeOH, DME; (f). i. Pd/C, HCOOH, MeOH; ii. LiOH, THF, water; (g). R¹NH₂, CDI, DMAc.

Scheme II above shows a general synthetic route for preparing compounds of the present invention when Ring A is imidazolyl ring g.

Reagents and conditions: (a).NH₂OH, DCM; (b). EtOCOCCH, xylene, Et₃N; (c). i, H₂, Pd/C, MeOH, ii, R¹NH₂, CDI, DMAc; iii) DIBAL-H, CH₂Cl₂, -78° C.; (d). TsOH, benzene, R²NH₂; (e). Tos-MIC, K₂CO₃, MeOH, DME.

Scheme III above shows a general synthetic route for preparing compounds of the present invention when Ring A is imidazolyl ring a.

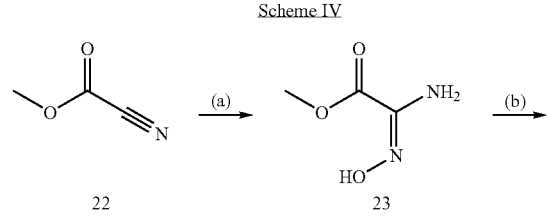

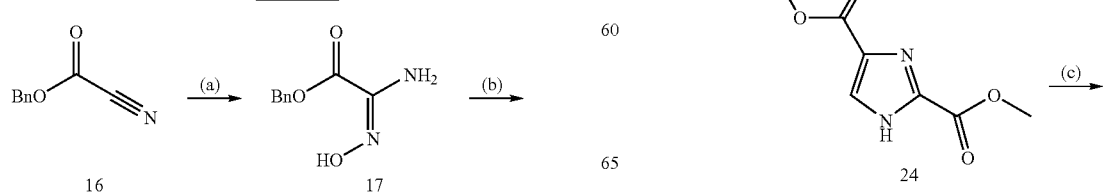

-continued

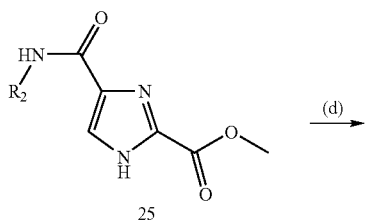
25

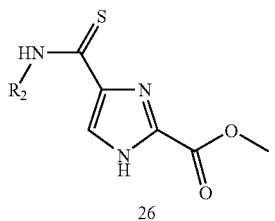
26

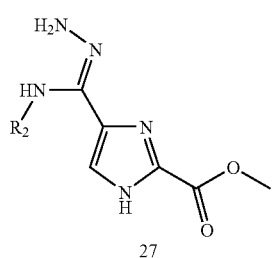
27

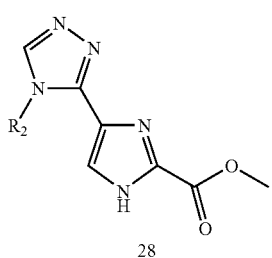
28

Reagents and conditions: (a). NH₂OH, DCM; (b). t-BuOCOCCH, xylene, Et₃N; (c). i, TFA, CH₂Cl₂, ii, R²NH₂, CDI, DMAc; (d). Lawesson's reagent, PhMe, reflux; (e). NH₂NH₂, EtOH/CH₂Cl₂; f). CH(OEt)₃, HCOOH.

Scheme IV above shows a general synthetic route for preparing compounds of the present invention when Ring A is triazolyl ring b. Compound 28 is then saponified to the carboxylate by the methods described above. The resulting carboxylate is coupled with a variety of groups, using methods known to one of ordinary skill in the art, to form a variety of compounds of the present invention.

Scheme V

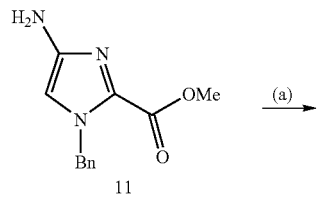
11

-continued

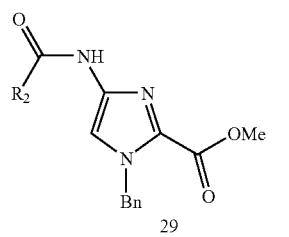
29

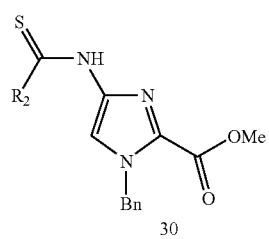
30

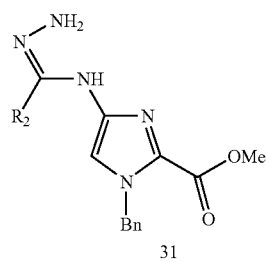
31

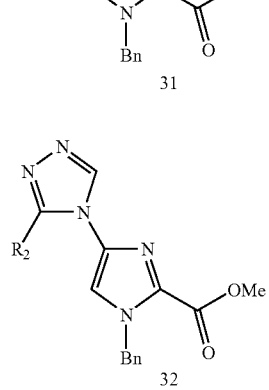
32

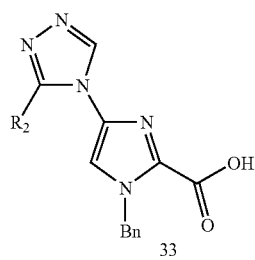
33

Reagents and conditions: (a). R²COCl, CH₂Cl₂; (b). Lawesson's reagent, PhMe, reflux; (c). NH₂NH₂, EtOH/CH₂Cl₂; (d). CH(OEt)₃, HCOOH; (e). i, Pd/C, HCOOH; ii, LiOH, THF, water Scheme V above shows an alternate route for preparing compounds of the present invention when Ring A is triazolyl ring b. The carboxylate 34 is coupled with a variety of groups, using methods known to one of ordinary skill in the art, to form a variety of compounds of the present invention.

Scheme VI

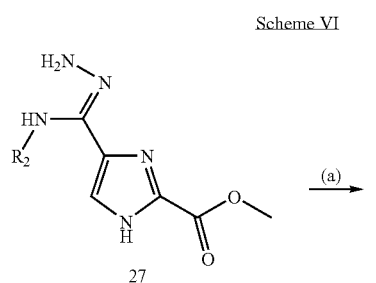

27

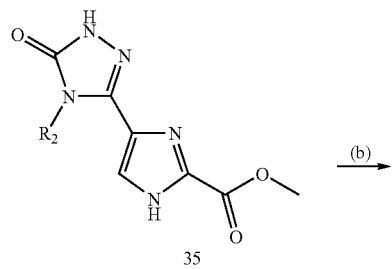

35

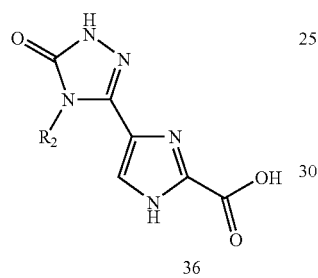

36

Reagents and conditions: a) i. EtOCOCl, Et3N, CH2Cl2, rt; ii. MeONa, MeOH, rt. b) 6N NaOH.

Scheme VI above shows a general synthetic route for preparing compounds of the present invention when Ring A is triazolyl ring b, substituted with oxo. The carboxylate 36 is coupled with a variety of groups, using methods known to one of ordinary skill in the art, to form a variety of compounds of the present invention.

Scheme VII

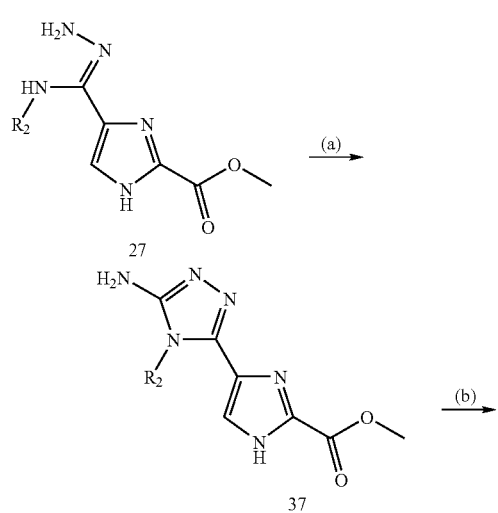

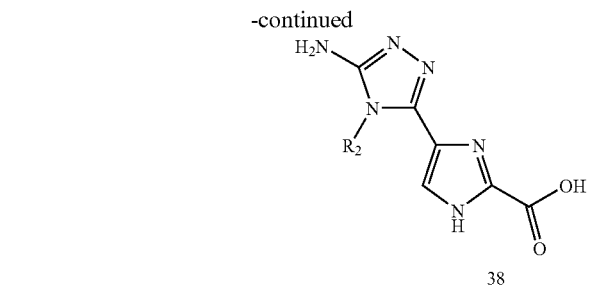

38

Reagents and conditions: a) BrCN, MeOH, rt. b) 6N NaOH.

Scheme VII above shows a general synthetic route for preparing compounds of the present invention when Ring A is triazolyl ring b, substituted with —NH2. The carboxylate 38 is coupled with a variety of groups, using methods known to one of ordinary skill in the art, to form a variety of compounds of the present invention.

Scheme VIII

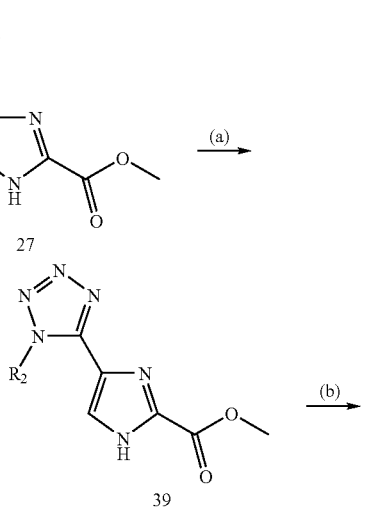

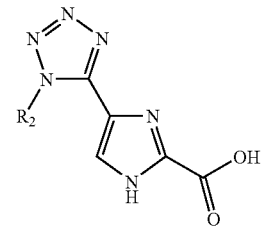

40

Reagents and conditions: a) NaNO2, HCl, rt; b) 6N NaOH.

Scheme VIII above shows a general synthetic route for preparing compounds of the present invention when Ring A is tetrazole ring d. The carboxylate 40 is coupled with a variety of groups, using methods known to one of ordinary skill in the art, to form a variety of compounds of the present invention.

Although certain exemplary embodiments are depicted and described above and herein, it will be appreciated that a compounds of the invention can be prepared according to the methods described generally above using appropriate starting materials by methods generally available to one of ordinary skill in the art. Accordingly, another embodiment of this invention provides processes for preparing compounds of formulas substantially as described above. It should be understood that these processes could employ other methods and other agents from those specifically depicted in Schemes I–VIII. For example, in Scheme VIII (b), the carboxylic acid can be obtained via hydrolysis of the ester under suitable conditions known to one skilled in the art. Although Scheme VIII depicts hydrolysis under basic conditions, other conditions conditions could also be employed in connection with this invention. Such conditions include acids (HCl, $H_2SO_4$), bases (NaOH, KOH), or other conditions known to one skilled in the art.

5. Uses, Formulation and Administration

The compounds and compositions described herein are generally useful for the inhibition of protein kinase activity of one or more enzymes. Further information relating to kinase structure, function and their role in disease or disease symptoms is available at the Protein Kinase Resource website.

Examples of kinases that are inhibited by the compounds and compositions described herein and against which the methods described herein are useful include, but are not limited to, c-Met, JAK, and KDR, and all subtypes of these kinases. The compounds and compositions of the invention are therefore also particularly suited for the treatment of diseases and disease symptoms that involve one or more of the aforementioned kinases.

The activity of a compound utilized in this invention as an inhibitor of c-Met, JAK, and/or KDR, may be assayed in vitro, in vivo or in a cell line. In vitro assays include assays that determine inhibition of either the phosphorylation activity or ATPase activity of activated c-Met, JAK, and/or KDR. Alternate in vitro assays quantitate the ability of the inhibitor to bind to c-Met, JAK, and/or KDR. Inhibitor binding may be measured by radiolabelling the inhibitor prior to binding, isolating the inhibitor/c-Met, inhibitor/JAK, or inhibitor/KDR, complex and determining the amount of radiolabel bound. Alternatively, inhibitor binding may be determined by running a competition experiment where new inhibitors are incubated with c-Met, JAK, and/or KDR bound to known radioligands. Detailed conditions for assaying a compound utilized in this invention as an inhibitor of c-Met, JAK, and KDR kinase are set forth in the Examples below.

According to another embodiment, the invention provides a composition comprising a compound of this invention or a pharmaceutically acceptable derivative thereof and a pharmaceutically acceptable carrier, adjuvant, or vehicle. The amount of compound in the compositions of this invention is such that is effective to detectably inhibit a protein kinase, particularly c-Met, JAK, and/or KDR kinase, in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "detectably inhibit", as used herein means a measurable change in c-Met, JAK, and/or KDR activity between a sample comprising said composition and a c-Met, JAK, and/or KDR kinase and an equivalent sample comprising c-Met, JAK, and/or KDR kinase in the absence of said composition.

As used herein, the term "JAK" is used interchangeably with the terms "JAK kinase" and "a JAK family kinase". In certain embodiments, JAK refers to JAK3 kinase.

As used herein, the term "c-Met" is used interchangeably with the terms "cMet", "MET", "Met", or other designations known to one skilled in the art.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of c-Met, JAK, and/or KDR kinase.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N+(C1–4 alkyl)4 salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01–100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting c-Met, JAK, and/or KDR kinase activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of protein kinase, or a protein kinase selected from c-Met, JAK, and/or KDR kinase, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting c-Met, JAK, and/or KDR kinase activity in a patient comprising the step of administering to said patient a compound of the present invention, or a composition comprising said compound.

The term "c-MET-mediated disease" or "c-MET-mediated condition", as used herein, means any disease state or other deleterious condition in which c-MET is known to play a role. The terms "c-MET-mediated disease" or "c-MET-mediated condition" also mean those diseases or conditions that are alleviated by treatment with a c-MET inhibitor. Such conditions include, without limitation, renal, gastric, colon, brain, breast, prostate, and lung cancer, atherosclerosis and lung fibrosis.

According to one embodiment, the present invention relates to a method of treating or lessening the severity of renal, colon, breast, prostate, or lung cancer, atherosclerosis or lung fibrosis in a patient in need thereof, comprising administering to said patient a compound of the present invention or composition thereof.

In an alternative embodiment, the present invention relates to a method of treating or lessening the severity of gastric or brain cancer in a patient in need thereof, comprising administering to said patient a compound of the present invention or composition thereof.

According to another embodiment, the present invention relates to a method of treating or lessening the severity of renal cancer in a patient in need thereof, comprising administering to said patient a compound of the present invention or composition thereof.

According to yet another embodiment, the present invention relates to a method of treating or lessening the severity of gastric cancer in a patient in need thereof, comprising administering to said patient a compound of the present invention or composition thereof.

Another aspect of the present invention relates to a method of inhibiting tumor metastasis in a patient in need thereof, comprising administering to said patient a compound of the present invention or composition thereof.

According to another embodiment, the invention provides a method for treating or lessening the severity of a JAK-mediated disease or condition in a patient comprising the step of administering to said patient a composition according to the present invention.

The term "JAK-mediated disease", as used herein means any disease or other deleterious condition in which a JAK family kinase is known to play a role. Accordingly, another embodiment of the present invention relates to treating or lessening the severity of one or more diseases in which JAK is known to play a role. Specifically, the present invention relates to a method of treating or lessening the severity of a disease or condition selected from immune responses such as allergic or type I hypersensitivity reactions, asthma, autoimmune diseases such as transplant rejection, graft versus host disease, rheumatoid arthritis, amyotrophic lateral sclerosis, and multiple sclerosis, neurodegenerative disorders such as Familial amyotrophic lateral sclerosis (FALS), as well as in solid and hematologic malignancies such as leukemias and lymphomas, wherein said method comprises administering to a patient in need thereof a composition according to the present invention.

According to another embodiment, the invention provides a method for treating or lessening the severity of a KDR-mediated disease or condition in a patient comprising the step of administering to said patient a composition according to the present invention.

The term "KDR-mediated disease", as used herein means any disease or other deleterious condition in which a KDR family kinase is known to play a role. Accordingly, another embodiment of the present invention relates to treating or lessening the severity of one or more diseases in which KDR is known to play a role. Specifically, the present invention relates to a method of treating or lessening the severity of a disease or condition selected from cancer such as brain cancer, genitourinary tract cancer, lymphatic system cancer, gastric cancer, cancer of the larynx, lung cancer, pancreatic cancer, breast cancer, Kaposi's sarcoma, and leukemia; endometriosis, benign prostatic hyperplasia; vascular diseases such as restenosis and atherosclerosis; autoimmune diseases such as rheumatoid arthritis and psoriasis; ocular conditions such as proliferative or angiogenic retinopathy and macular degeneration; and inflammatory diseases such as contact dermatitis, asthma and delayed hypersensitivity reactions.

Depending upon the particular condition, or disease, to be treated, additional therapeutic agents, which are normally administered to treat that condition, may also be present in the compositions of this invention. As used herein, additional therapeutic agents that are normally administered to treat a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the inhibitors of this invention may also be combined with include, without limitation: treatments for Alzheimer's Disease such as Aricept(D and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Those additional agents may be administered separately from the compound-containing composition, as part of a multiple dosage regimen. Alternatively, those agents may be part of a single dosage form, mixed together with the compound of this invention in a single composition. If administered as part of a multiple dosage regime, the two active agents may be submitted simultaneously, sequentially or within a period of time from one another normally within five hours from one another.

The amount of both, the compound and the additional therapeutic agent (in those compositions which comprise an additional therapeutic agent as described above)) that may be combined with the carrier materials to produce a single dosage form will vary depending upon the host treated and the particular mode of administration. Preferably, the compositions of this invention should be formulated so that a dosage of between 0.01–100 mg/kg body weight/day of a compound of formula I can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01–100 mg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition. Implantable devices coated with a compound of this invention are another embodiment of the present invention.

In order that the invention described herein may be more fully understood, the following examples are set forth. It should be understood that these examples are for illustrative purposes only and are not to be construed as limiting this invention in any manner.

SYNTHETIC EXAMPLES

As used herein, the term "$R_t$(min)" refers to the HPLC retention time, in minutes, associated with the compound. Unless otherwise indicated, the HPLC method utilized to obtain the reported retention time is as follows:

Column: Zorbax SB C18 column, 3.0×150 mm
Gradient: 10–90% acetonitrile+water (0.1% TFA)
Flow rate: 1.0 mL/minute
Detection: 254 & 214 nm.

Example 1

2-(2,5-Dihydro-pyrrole-1-carbonyl)-1H-imidazole-4-carboxylic acid ethyl ester: 1H-Imidazole-2,4-dicarboxylic acid 2-benzyl ester 4-ethyl ester was prepared in a manner substantially similar to that described by Branco, P. S.; Prabhakar, S.; Lobo, A. M.; Williams, D. Tetrahedron, 1992, 48, 6335. To a solution of 1H-imidazole-2,4-dicarboxylic acid 2-benzyl ester 4-ethyl ester (380 mg, 1.4 mmol) in EtOH (10 mL) was added Pd/C (10%) (40 mg) under $N_2$ atmosphere. The suspension was then treated with hydrogen under 50 psi for 3 hours. The catalyst was removed by filtration through Celite® and the filtrate was evaporated. To a solution of the crude acid (140 mg, 0.76 mmol) in DMA (2 mL) was added CDI (140 mg, 0.86 mmol). The mixture was stirred at ambient temperature for 1 hour and then 2,5-dihydro-1H-pyrrole (110 mg, 1.59 mmol) was added. After stirring at ambient temperature for 2 hours, the reaction mixture was poured into water (5 mL). The aqueous solution was extracted with EtOAc (2×10 mL) and the combined organic layers dried over $MgSO_4$, filtered, and evaporated. The crude product was purified by flash column eluting with 50% EtOAc in hexane to afford the title compound as a white solid (110 mg, 61%). MS (ES+): m/e=236.2 (M+H); $R_t$=2.04 minutes.

Example 2

2-(2,3-Difluoro-phenyl)-1-[2-(2,5-dihydro-pyrrole-1-carbonyl)-1H-imidazol-4-yl]-ethanone: To a mixture of 2-(2,5-dihydro-pyrrole-1-carbonyl)-1H-imidazole-4-carboxylic acid ethyl ester (100 mg, 0.43 mmol) and (2,3-difluoro-phenyl)acetic acid (75 mg, 0.44 mmol) in anhydrous THF (5 mL) was added LDMS (1.0M in THF, 1.5 mL, 1.5 mmol) at −78° C. After addition of LDMS, the dry-ice bath was removed and the reaction was stirred at ambient temperature for 6 hours. To this reaction mixture was added 1 mL of sat. $NH_4Cl$ solution and EtOAc then the organic layer was separated and dried over $MgSO_4$. After removal of solvent, the residue was washed with water to afford the title compound as a yellow solid. This crude product was used directly for the next step without further purification. MS (ES+): m/e=318.2 (M+H); $R_t$=3.21 minutes.

Example 3

{4-[4-(2,3-Difluoro-phenyl)-isoxazol-5-yl]-1H-imidazol-2-yl}-(2,5-dihydro-pyrrol-1-yl)-methanone (I-38): $^1$H NMR (500 MHz, DMSO-d6) δ 13.55 (s, 1H), 8.86 (s, 1H), 7.89 (s, 1H), 7.48 (m, 2H), 7.30 (q, 1H), 5.92 (d, 1H), 5.86 (d, 1H), 4.37 (s, 2H), 4.25 (s, 2H). M+343.1. M-341.2. $R_t$=3.43 minutes.

Example 4

$K_i$ Determination for the Inhibition of c-Met

Compounds were screened for their ability to inhibit c-Met kinase activity using a standard coupled enzyme system (Fox et al., Protein Sci. 1998, 7, 2249). Reactions were carried out in a solution containing 100 mM HEPES (pH 7.5), 10 mM $MgCl_2$, 25 mM NaCl, 300 µM NADH, 1 mM DTT, and 1.5% DMSO. Final substrate concentrations in the assay were 200 μM ATP (Sigma Chemicals, St Louis, Mo.) and 10 μM polyGluTyr (Sigma Chemical Company, St. Louis). Reactions were carried out at 30° C. and 80 nM c-Met. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above with the exception of ATP and a test compound of the present invention. The assay stock buffer solution (175 μl) was incubated in a 96 well plate with 5 μl of the test compound of the present invention at final concentrations spanning 0.006 μM to 12.5 μM at 30° C. for 10 minutes. Typically, a 12-point titration was conducted by preparing serial dilutions (from 10 mM compound stocks) with DMSO of the test compounds of the present invention in daughter plates. The reaction was initiated by the addition of 20 μl of ATP (final concentration 200 μM). Rates of reaction were obtained using a Molecular Devices Spectramax plate reader (Sunnyvale, Calif.) over 10 minutes at 30° C. The $K_i$ values were determined from the rate data as a function of inhibitor concentration.

Compounds of the present invention were found to be inhibitors of c-Met. Compound I-38 was found to inhibit c-Met with a $K_i$ value <1 μM.

Example 5

JAK Inhibition Assays

JAK3 Assay Components:
 kinase buffer: (100 mM HEPES pH 7.4; 1 mM DTT; 10 mM $MgCl_2$; 25 mM NaCl; and 0.01% BSA)
 1 nM JAK3 (enzyme)
 1 uM poly(Glu)$_4$Tyr (substrate)
 5 uM ATP (substrate, 200 uCi/umole ATP)

Procedure

To each well of a 96 well polycarbonate plate is added 1.5 ul of a candidate JAK3 inhibitor along with 50 ul of kinase buffer containing 2 uM poly(Glu)$_4$Tyr and 10 uM ATP. This is then mixed and 50 ul of kinase buffer containing 2 nM JAK3 enzyme is added to start the reaction. After 20 minutes at room temperature (25C), the reaction is stopped with 50 ul of 20% trichloroacetic acid (TCA) that also contains 0.4 mM ATP. The entire content of each well is then transferred to a 96 well glass fiber filter plate using a TomTek Cell Harvester. After washing, 60 ul of scintillation fluid is added and 33P incorporation detected on a Perkin Elmer TopCount.

Compounds of the present invention were found to be inhibitors of JAK3. Compound I-38 was found to inhibit JAK3 with a $K_i$ value <1 μM.

JAK2 Assay:
 As above except that final poly(Glu)$_4$Tyr concentration is 15 uM and final ATP concentration is 12 uM.

Example 6

KDR Enzyme Assay

Compounds were screened for their ability to inhibit KDR using a standard coupled enzyme assay (Fox et al., Protein Sci., (1998) 7, 2249). Assays were carried out in a mixture of 200 mM HEPES 7.5, 10 mM $MgCl_2$, 25 mM NaCl, 1 mM DTT and 1.5% DMSO. Final substrate concentrations in the assay were 300 μM ATP (Sigma Chemicals) and 10 μM poly E4Y (Sigma). Assays were carried out at 37° C. and 30 nM KDR. Final concentrations of the components of the coupled enzyme system were 2.5 mM phosphoenolpyruvate, 200 μM NADH, 30 μg/ML pyruvate kinase and 10 μg/ml lactate dehydrogenase.

An assay stock buffer solution was prepared containing all of the reagents listed above, with the exception of ATP and the test compound of interest. 177 μl of the stock solution was placed in a 96 well plate followed by addition of 3 μl of 2 mM DMSO stock containing the test compound (final compound concentration 30 μM). The plate was preincubated for about 10 minutes at 37° C. and the reaction initiated by addition of 20 μl of ATP (final concentration 300 μM). Rates of reaction were obtained using a Molecular Devices plate reader (Sunnyvale, Calif.) over a 5 minute read time at 37° C. Compounds showing greater than 50% inhibition versus standard wells containing the assay mixture and DMSO without test compound were titrated to determine IC50 values determined.

Compounds of the present invention were found to be inhibitors of KDR. Compound I-38 was found to inhibit KDR with a $K_i$ value <5 μM.

All documents cited herein are incorporated by reference. While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

What is claimed is:

1. A compound of formula I:

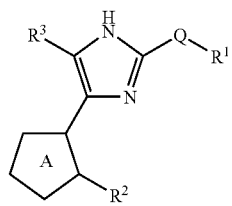

or a pharmaceutically acceptable salt thereof, wherein:
 Q is a $C_{1-6}$ alkylidene chain wherein one methylene unit of Q is replaced by —C(O)N(R)—, —C(O)—, —C(O)O—, —N(R)—, —O—, —S—, —$SO_2$—, or —$SO_2$N(R)—;
 each R is independently hydrogen or an optionally substituted $C_{1-6}$ aliphatic group, wherein:
  two R groups on the same nitrogen atom are optionally taken together with said nitrogen atom to form an optionally substituted 3–7 membered saturated, partially unsaturated, or fully unsaturated ring having 1–3 heteroatoms independently selected from nitrogen, oxygen, or sulfur;
 $R^1$ is H, —N(R)$_2$, or an optionally substituted ring selected from a 3–7 membered saturated or partially unsaturated ring having 0–3 heteroatoms independently selected from nitrogen, oxygen, or sulfur; a 5–6 membered aryl ring having 0–4 heteroatoms independently selected from nitrogen, oxygen, or sulfur; or an 8–10 membered bicyclic partially unsaturated or aryl ring having 0–4 heteroatoms independently selected from nitrogen, oxygen, or sulfur;

R² is an optionally substituted 6-membered aryl ring having 0–3 nitrogens;

R³ is R, CN, NO₂, halogen, N(R)₂, OR, or SR; and

Ring A is an optionally substituted ring selected from:

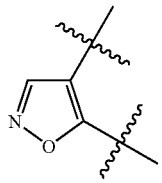
e

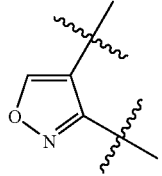
f

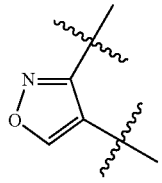  or
o

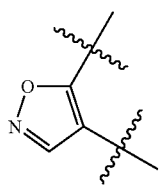
p

2. The compound according to claim 1, wherein Q is a $C_{1-6}$ alkylidene chain wherein one methylene unit of Q is replaced by —C(O)— or —C(O)N(R)—.

3. The compound according to any one of claims 1, wherein Q is a $C_1$ alkylidene chain wherein the methylene unit is replaced by —C(O)N(R)—.

4. The compound according to any one of claims 1, wherein, Q is a $C_1$ alkylidene chain wherein the methylene unit is replaced by —C(O)N(R)—.

5. The compound according to any one of claims 1, wherein R¹ is an optionally substituted ring selected from a 3–7 membered saturated or partially unsaturated ring having 0–3 heteroatoms independently selected from nitrogen, oxygen, or sulfur; a 5–6 membered aryl ring having 0–4 heteroatoms independently selected from nitrogen, oxygen, or sulfur; or an 8–10 membered bicyclic partially unsaturated or aryl ring having 0–4 heteroatoms independently selected from nitrogen, oxygen, or sulfur.

6. The compound according to any one of claims 1, wherein R¹ is a 4–6 membered saturated ring having 0–3 heteroatoms independently selected from nitrogen, oxygen, or sulfur.

7. The compound according to any one of claims 1, wherein R¹ is cyclopentyl, cyclohexyl, tetrahydrofuranyl, pyrrolidin-1-yl, morpholin-4-yl, thiomorpholin-4-yl, piperidin-1-yl, or azetidin-1-yl.

8. The compound according to any one of claims 1, wherein R¹ is a 4–6 membered partially saturated ring having 0–3 heteroatoms independently selected from nitrogen, oxygen, or sulfur.

9. The compound according to any one of claims 8, wherein R¹ is cyclopentenyl.

10. The compound according to any one of claims 1, wherein R¹ is a 5–6 membered aryl ring having 0–4 heteroatoms independently selected from nitrogen, oxygen, or sulfur or an 8–10 membered bicyclic partially unsaturated or aryl ring having 0–4 heteroatoms independently selected from nitrogen, oxygen, or sulfur.

11. The compound according to any one of claims 1, wherein R² is an optionally substituted phenyl ring.

12. The compound according to any one of claims 1, wherein R² is an optionally substituted pyridyl or pyrimidinyl ring.

13. The compound according to any one of claims 1, wherein Ring A is selected from:

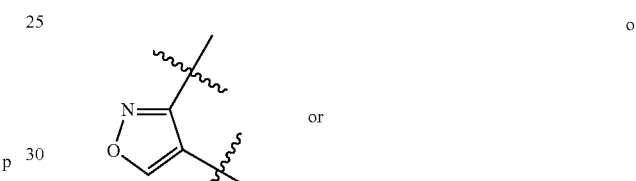  or
o

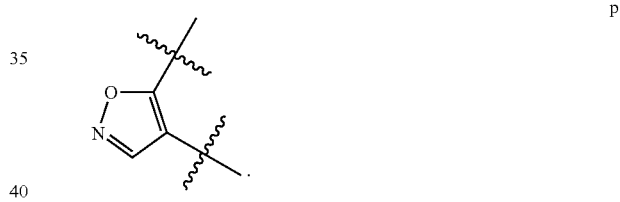
p

14. A compound selected from the group consisting of:

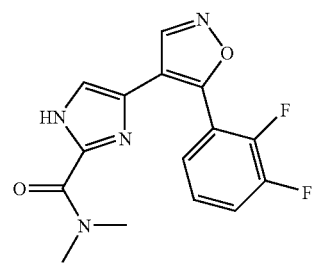
I-1

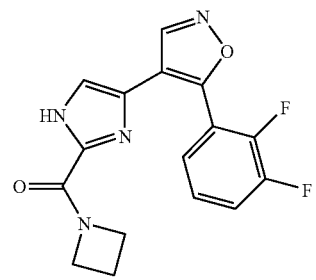
I-2

-continued
I-3
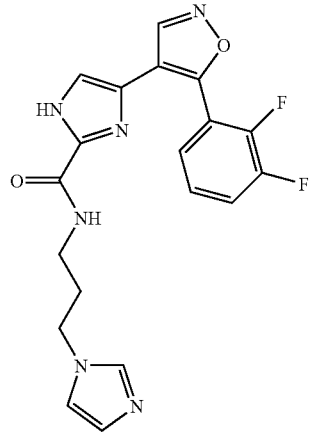
I-7
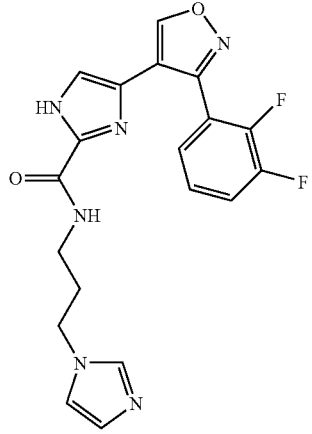
I-4
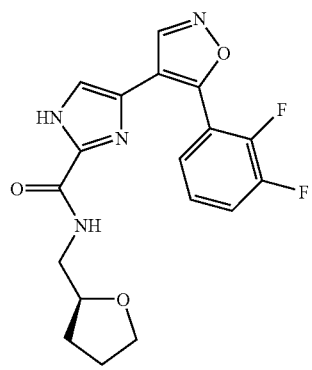
I-8
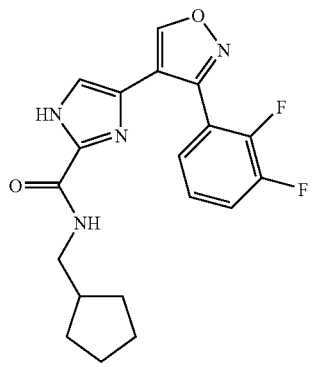
I-5
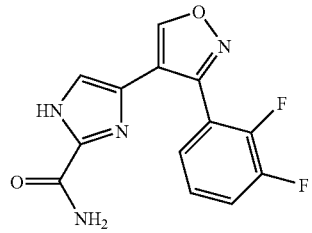
I-37
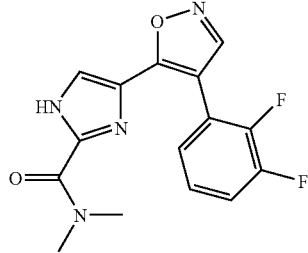
I-6
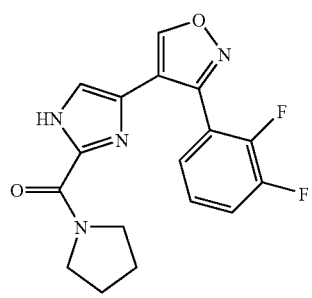
I-38
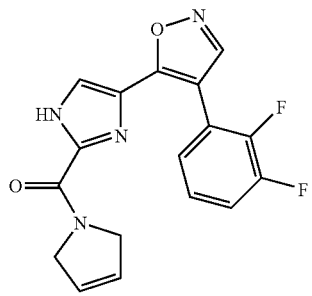

-continued

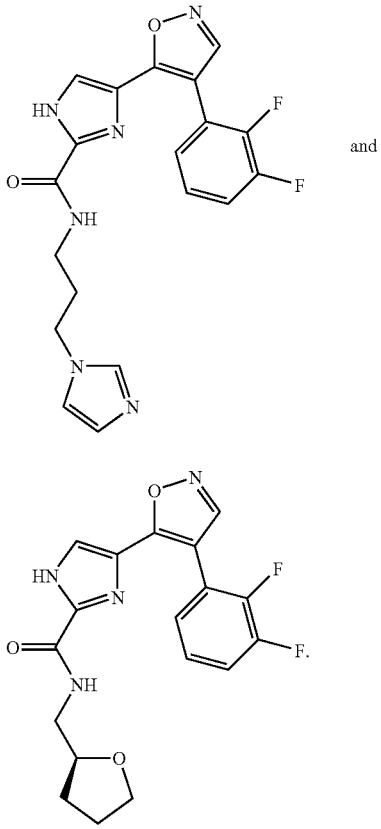

I-39 and

I-40

15. A composition comprising an effective amount of a compound according to claim 1, and a pharmaceutically acceptable carrier, adjuvant, or vehicle.

16. The composition according to claim 15, wherein said compound is in an amount sufficient to detectably inhibit c-Met, JAK, or KDR protein kinase activity.

17. A method of inhibiting c-Met, JAK, or KDR protein kinase activity in a biological sample, which method comprises contacting said biological sample *in vitro* with a composition according to claims 15 or a compound according to claims 1.

18. A method of treating or lessening the severity of a cancer or a proliferative disorder in a patient in need thereof, wherein said cancer or proliferative disorder is selected from glioblastoma, gastric carcinoma, colon cancer, renal cancer, breast cancer, prostate cancer, cancer of the brain, liver cancer pancreatic cancer, or lung cancer, said method comprising the step of administering to said patient a composition according to claims 15 or a compound according to claims 1.

19. The method according to claims 18 comprising the additional step of administering to said patient an additional therapeutic agent selected from imatinib mesylate, adriamycin, dexamethasone, vincristine, cyclophosphamide, fluorouracil, topotecan, taxol, an interferon, or a platinun derivative, wherein said additional therapeutic agent is administered together with said composition as a single dosage form or separately from said composition as part of a multiple dosage form.

20. The method according to claim 18 wherein said cancer or proliferative disorder is renal cancer.

21. The method according to claim 18, wherein said cancer or proliferative disorder is gastric carcinoma.

22. The method according to claim 18, wherein said cancer or proliferative disorder is glioblastoma, or a cancer selected from breast, colon, or liver cancer.

23. A method of inhibiting tumor metastasis in a patient, comprising administering to said patient a composition according to claim 15 or a compound according to claim 1.

24. A method of treating asthma in a patient in need thereof, comprising administering to said patient a composition according to claim 15 or a compound according to claim 1.

* * * * *